(12) United States Patent
Jacobson et al.

(10) Patent No.: US 6,953,659 B2
(45) Date of Patent: Oct. 11, 2005

(54) DIRECT, EXTERNALLY IMPOSED CONTROL OF NUCLEIC ACIDS

(75) Inventors: Joseph M. Jacobson, Newton, MA (US); John J. Schwartz, Newtonville, MA (US); Kimberly Hamad, Cambridge, MA (US); Shuguang Zhang, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/905,832

(22) Filed: Jul. 13, 2001

(65) Prior Publication Data

US 2002/0061588 A1 May 23, 2002

Related U.S. Application Data

(60) Provisional application No. 60/276,388, filed on Mar. 16, 2001, and provisional application No. 60/218,312, filed on Jul. 14, 2000.

(51) Int. Cl.[7] .......................... C12Q 1/68; C12P 19/34; C07H 21/00; C07H 21/02
(52) U.S. Cl. .......................... 435/6; 435/7.1; 435/91.1; 435/91.2; 435/287.2; 536/22.1; 536/23.1; 536/24.3; 536/24.33
(58) Field of Search .......................... 435/6, 7.1, 91.1, 435/91.2, 287.1; 536/221, 23.1, 24.3–24.33

(56) References Cited

U.S. PATENT DOCUMENTS

| | | | | |
|---|---|---|---|---|
| 5,283,174 A | * | 2/1994 | Arnold, Jr. et al. | 435/6 |
| 6,410,235 B1 | * | 6/2002 | Weindel et al. | 435/6 |
| 6,506,564 B1 | * | 1/2003 | Mirkin et al. | 435/6 |
| 2002/0165191 A1 | * | 11/2002 | Moonen | 514/44 |

OTHER PUBLICATIONS

Kellogg et al Biotechniques vol. 16 No. 6 pp. 1134–1138 1994.*

* cited by examiner

*Primary Examiner*—Jezia Riley
(74) *Attorney, Agent, or Firm*—Norma E. Henderson (57) ABSTRACT

Methods and compositions for rendering nucleic acids directly responsive to an external signal utilizing modulators that themselves respond to the external signal and are associated with the nucleic acid. In response to the external signal, the modulator alters physical properties of the specific nucleic acid molecule(s) with which it is associated, thereby altering the structural and functional properties thereof. The modulator may, for example, transfer applied energy to a nucleic acid, or to a portion of the nucleic acid, thereby changing the nucleic acid structure.

30 Claims, 8 Drawing Sheets

(SEQ ID NO. 1)

DIRECT, EXTERNALLY IMPOSED CONTROL OF NUCLEIC ACIDS

RELATED APPLICATIONS

This application claims priority to, and the benefit of U.S. Provisional Patent Application Ser. No. 60/276,388 filed on Mar. 16, 2001, and Ser. No. 60/218,312 filed on Jul. 14, 2000, the disclosures of which are incorporated by reference herein.

STATEMENT REGARDING FEDERALLY SPONSORED RESEARCH

This invention was made with U.S. government support under Grant Number DAAD16-01-C-0048, awarded by the Army. The government has certain rights in this invention.

FIELD OF INVENTION

The present invention relates to methods and compositions for controlling biological reactions through the use of external electric or magnetic fields or optical pulses. In particular, the invention relates to methods and compositions for controlling the structural and functional properties of nucleic acids.

BACKGROUND

Known methods for altering the structure of a nucleic acid typically involve changing the physical conditions of a sample that contains the nucleic acid. The sample may be heated or cooled, or the pH or salt concentration of the sample may be varied. Any one of these changes may affect the structure of a nucleic acid. However, because they are applied globally, such changes may also affect the structures of other components of the sample. Consequently, the functional properties of all biomolecules in the sample may be affected.

Conventional techniques are also global with respect to the nucleic acid molecule itself, affecting the molecule as a whole rather than a localized portion thereof. For example, the effects of a gross environmental change, such as heating, will affect the entire molecule uniformly. Even chemical reagents directed toward particular moieties will affect such moieties wherever they occur along the molecule. As a result, precise control over individual molecular entities or portions thereof has not heretofore been feasible.

Nonetheless, in many practical settings there is a need to control the function of a specific nucleic acid that is present in a heterogeneous solution containing other nucleic acids and proteins. There is also a need in the art for methods and compositions for directly or remotely altering the properties of a nucleic acid, or a portion of a nucleic acid without changing any other components of a sample containing the nucleic acid.

SUMMARY OF THE INVENTION

The invention provides methods and compositions for rendering nucleic acids locally and directly responsive to an external signal. A nucleic acid in accordance with the invention is characterized by structural and functional properties that facilitate regulation by an external signal that does not directly affect other nucleic acids. In addition, the signal may only affect one or more specific, localized portions of the nucleic acid. According to the invention, an external signal alters a property of a specific nucleic acid thereby changing its function. Consequently, the invention provides methods and compositions for regulating the structure and function of a nucleic acid (or portion thereof) in a biological sample, without affecting the properties of other components of the sample (or portions of the molecule remote from the affected region).

According to the invention, a modulator that is responsive to an external signal is associated with a nucleic acid. In one embodiment of the invention, the modulator includes or behaves as an antenna. In a preferred embodiment of the invention, the antenna is a nanometer-scale antenna covalently linked to a nucleic acid. In response to the external signal, the modulator alters physical properties of the specific nucleic acid molecule(s) with which it is associated, thereby altering the structural and functional properties thereof. In a preferred embodiment, the modulator transfers applied energy to a nucleic acid, or to a portion of the nucleic acid, thereby changing the nucleic acid structure. In a particularly preferred embodiment, the modulator transfers heat to a nucleic acid or portion thereof, resulting, for example, in the destabilization of inter- or intramolecular bonds and causing the structure or stability of the nucleic acid to change. In an alternative embodiment of the invention, a modulator cools the nucleic acid with which it is associated also causing a change in the structure or stability of the nucleic acid.

According to the invention, the modulator only affects the nucleic acid with which it is associated, and not other components of a sample, such as other nucleic acids or proteins in a biological sample. In preferred embodiments of the invention, a modulator is covalently attached to a nucleic acid. A modulator may be attached to the 3' end of a nucleic acid, the 5' end of a nucleic acid, or to an internal nucleotide of a nucleic acid. A modulator may be associated with a particular nucleic acid portion to be controlled. In one embodiment, a modulator is associated with a nucleic acid in a 1:1 ratio. In a preferred embodiment, one modulator is present for approximately every 10 kb of a nucleic acid, and more preferably for every 1 kb, and most preferably for every 500 bp.

In general, a modulator in accordance with the invention is active only when it is exposed to an external field, e.g., a magnetic, electric, or electromagnetic field. Preferred modulators are organic or inorganic materials that are responsive to the applied external field. Preferred modulators include metal nanoparticles, semiconducting nanoparticles, magnetic nanoparticles, oxide nanoparticles, and chromophores. In particularly preferred embodiments of the invention, a modulator comprises one or more of colloidal or non-colloidal gold, silicon, ruthenium, cadmium selenide, or composites of such materials in various morphologies (such as core-shell structures).

In some embodiments of the invention, a single type of modulator is associated with a nucleic acid. Alternatively, two or more different modulators may be associated with a single nucleic acid. The different modulators are preferably responsive to different signals. For example, two modulators may be of different types in that one is a chromophore and the other is a metal nanoparticle. Alternatively, the different modulators may be of the same type, but responsive to different signals. For example the modulators may be different chromophores that are responsive to different wavelengths. Alternatively, the modulators may be nanoparticles of different sizes with different resonant frequencies.

A modulator may be associated with a nucleic acid by mixing a modulator preparation with a nucleic acid preparation, preferably in solution. A modulator is preferably linked to a specific nucleic acid, most preferably via a covalent bond. A modulator may be provided in a form that interacts directly with a nucleic acid to form a modified nucleic acid linked to the modulator. Alternatively, the modulator may be provided in a form that is incorporated into a nucleic acid during synthesis. For example, the modulator may be provided as a modified phosphoramidite that is incorporated into a synthetic nucleic acid. Alternatively, the modulator may be provided as a modified nucleotide that is incorporated into a nucleic acid in an enzyme-catalyzed reaction, such as a template-based DNA or RNA polymerization reaction. In preferred embodiments, a modulator is associated with a nucleic acid in vitro. However, in alternative embodiments, a modulator is associated with a nucleic acid in vivo in a cell culture or in cells of a patient. A modulator may also be self-assembled onto a peptide, or on aptamers associated with a target molecule.

Modulators of the invention are useful to remotely control reactions involving nucleic acids. In preferred embodiments of the invention, a modulator is useful to regulate nucleic acid hybridization, DNA/protein interactions, RNA/protein interactions, PNA/protein interactions, DNA replication, transcription, reverse transcription, or RNA translation. Modulators are also useful to regulate enzymatic reactions catalyzed by nucleic acid-based enzymes such as ribozymes.

In one embodiment, a modulator is used to regulate antisense mediated inhibition of gene expression. The modulator may be associated with an antisense nucleic acid, such as an antisense RNA. The antisense nucleic acid inhibits translation of a specific mRNA by binding to specific sequences within the mRNA. According to the invention, an external field interacts with the modulator so as to reduce the affinity of the modified antisense nucleic acid for its targeted mRNA binding site, thereby reducing its inhibitory effect. In an alternative embodiment, a modulator attached to a strand-invasive transcription-blocking PNA oligomer is useful for external regulation of gene expression. Accordingly, the invention may be used to regulate gene expression, in vivo or in vitro. Moreover, because the addressing is not optical, this technology is useful in systems that do not facilitate visual or optical observation, e.g., dispersions in highly scattering media.

In another embodiment, a modulator is used in a nucleic-acid amplification reaction such as a DNA amplification reaction. Stimulation of the modulator may substitute for heating the amplification sample to denature extended primer products during the amplification cycle. In preferred embodiments of the invention, amplification primers are modified to contain a modulator. In particularly preferred embodiments, a modulator is incorporated into the amplified product in the form of a modified nucleotide that is linked to a modulator.

The invention also extends to devices that are useful in exposing a nucleic acid sample to an external field. In a preferred embodiment, an apparatus of the invention includes an external field generator and a sample well that is configured to receive a nucleic acid sample to be exposed to the external field. The sample is provided in a container that is configured for the apparatus. The invention also provides a handheld device that is useful to expose a nucleic acid sample, in vitro or in vivo, to a desired external field.

Finally, the invention can be used to read out the state of a molecular system or the action of a control input into a molecular system.

BRIEF DESCRIPTION OF THE DRAWINGS

FIG. 4 depicts control of a nucleic-acid nano-assembler using modulators. The modulator is attached to a series of "modules (labeled 1, 2, 3)," which are peptides or nucleic acids strung together in a specific order. The nucleic acid to be modified travels down the modules in order. Its transfer from module to module is dictated by when the user addresses the modular by electromagnetic, magnetic, optical, or other physical means.

DETAILED DESCRIPTION OF THE PREFERRED EMBODIMENTS

1. Modulator Association a. Modulators

A modulator in accordance with the invention absorbs energy, which may be broadcast as a signal, and transfers or transduces this energy to the associated nucleic-acid molecule. The applied energy is generally magnetic, electric, or electromagnetic in nature, and may be, for example, a magnetic field, a radio-frequency (RF) or other broadcast signal, or optical radiation (e.g., visible, infrared, or ultraviolet light). Accordingly, a modulator is chosen for sensitivity to a preferred energy signal. Certain metals (e.g., gold, in colloidal or non-colloidal form, silver, copper,), magnetic materials (e.g. iron oxide), and semiconductors (e.g., silicon, cadmium selenide, cadmium sulfide, cadmium telluride, indium phosphide, indium arsenide, gallium arsenide) are responsive to RF and/or optical energy and, when covalently linked as nanoparticles to a nucleic acid, are capable of transferring applied energy to the nucleic-acid molecule. For example, the excitation field may heat the particle and, consequently, its immediate environment; if sufficiently localized, the effects of the heat are confined to the nucleic acid or a portion thereof.

Chromophores integral with or constituting a nanoparticle can also be associated with a nucleic acid, transferring energy when stimulated by radiation that they absorb. Preferred chromophores respond to optical radiation in a photochemical process involving election transfer (for example the chromophore Ru(bipyridine)$_3$ which can initiate folding of cytochrome C.) Magnetic materials (such as the Ferro V magnetic pigment) transduce energy when exposed to a magnetic field of sufficient intensity; for example, an alternating magnetic field will induce an alternating current in the particle, producing heat. According to the invention, other metal or magnetic materials, such as $Fe_3O_4$, $Fe_2O_3$, silver, copper, platinum, palladium can also be modulators.

It is frequently found that modulators are responsive over a range of frequencies, but provide maximal energy transduction at a single frequency or narrow range of frequencies. For example, chromophores tend to exhibit a peak absorption wavelength ($\lambda_{max}$). Similarly, nanocrystals sensitive to RF and magnetic fields may exhibit resonance behavior. This behavior may be size-dependent, with larger particles, for example, having lower resonance frequencies than smaller particles.

Modulators may be employed to reduce temperature—i.e., to withdraw energy from the immediately surrounding environment rather than to impart it. To achieve this, a magnetic nanoparticle may be attached to a nucleic acid of interest and employed in a superparamagnetic cooling arrangement. The magnetic moment of the nanoparticle is first polarized in a magnetic field and then allowed to dephase using energy contained in the nucleic acid, thus cooling the nucleic acid. In order to achieve efficient cooling, the magnetic nanoparticle should be thermally decoupled from the nucleic acid during the polarization step. This may be accomplished, for example, by initially breaking a bond between the nanoparticle the nucleic acid (e.g., using a laser or other radiation source), subjecting the particle to magnetic polarization, and then allowing the bond to reform.

b. Associating a Modulator with a Nucleic Acid

In general, modulators are associated with nucleic acids covalently, e.g., through selective incorporation of a reactive nucleotide capable of binding with the modulator. In this way, the modulator may be associated with the nucleic acid at one or more predetermined sites. The ability to preferentially locate the modulator along the nucleotide chain facilitates transduction of applied energy at these sites. In some cases, it is desired to concentrate energy at these specific sites. In other cases the intention is to affect the nucleic acid as a whole, in which case the modulators may be spread along the length of the nucleic acid in order to distribute applied energy throughout the molecule, or, in the case of relatively small oligomers, placed only at the 5' and/or the 3' end.

For example, sulfhydryl groups incorporated within nucleic-acid residues will react directly with colloidal gold and cadmium selenide particles and other particles including inorganic particles such as metals (e.g. silver, copper), magnetic materials (e.g. cobalt, iron oxide) semiconductors (e.g. cadmium sulfide, cadmium telluride, zinc selenide, zinc sulfide, indium phosphide, indium arsenide, gallium arsenide) insulators (e.g. titanium oxide, barium titanate, zinc oxide), forming covalent bonds therewith. Alternatively, sulfhydryl groups will form covalent bonds with nanoparticles that have appropriate functionality (e.g., maleimide) incorporated into a ligand on the surface of the particle; a suitable monomaleimido gold particle is supplied, for example, by Nanoprobes, Yaphank, N.Y. under the trade name NANOGOLD; these particles have mean diameters of 1.4 nm±10%.

Nanoparticles can also be provided with functionality (e.g., N-hydroxysuccinimidyl ester) capable of reacting with amine groups associated with nucleic-acid residues. For example, a suitable sulfo-N-hydroxysuccinimido NANOGOLD particle is also supplied by Nanoprobes. Other examples of amine reactive ligands are isocyanates, acyl azides, sulfonyl chlorides, epoxides, oxiranes, carbodiimides, anhydrides.

Selective incorporation within a nucleic acid is achieved by associating complementary chemical functionality with specific residues, so that only these residues react covalently with the nanoparticles. For example, an amine- or sulfhydryl-modified nucleotide may be incorporated within the nucleic-acid backbone by any of various techniques as discussed below. A suitable, commercially available amine-functional nucleotide is 5-(3-aminoallyl)-dUTP. The modified nucleotide may be reacted with a nanoparticle having complementary functionality either before or after the nucleotide is introduced into the nucleic-acid chain.

For oligomers that are synthesized directly, the functionalized nucleotide is simply incorporated during synthesis at the desired location or locations in the growing chain. In the case of phosphoramidite chemosynthesis, for example, the modulator (or modulator binding group) may be incorporated as a modified phosphoramidite. Alternatively, the modulator may be inserted into an existing nucleic acid, e.g., by means of an enzyme-catalyzed reaction. If only a single modulator is necessary, or if several modulators can be clustered together, they may be added to the 3' or 5' terminus. For example, an allylamine-dUTP may be added to the end of a nucleic acid using conventional techniques such as template-directed polymerase extension, deoxynucleotidyl terminal transferase extension with biotin, or other suitable extension technique. Such reactions may occur in vivo or in vitro.

Oligomers containing one or more modulators (or sites to which modulators can subsequently be bound) can be inserted into nucleic acids using restriction endonucleases. For example, a double-stranded oligomer that contains the modulator and is complementary to the restriction fragments created through cleavage by a particular restriction endonuclease can be synthesized either directly, as a polylinker, or through cleavage with the same endonuclease. In the presence of DNA ligase, the oligomer is incorporated into the nucleic-acid chain at the restriction site.

2. Applications

In one application, the modulator facilitates on-demand melting or dehybridization of a double-stranded nucleic-acid polymer. When subject to, for example, optical or RF magnetic fields, the modulator-containing nucleic acid melts, but the surrounding environment (including nucleic acids lacking modulators) is substantially unaffected. The ratio of modulator nanoparticles to base pairs necessary to reliably effect melting depends on various factors, including the transduction efficiency of the modulator-nucleic acid system and the intensity of the applied field. In general, it is preferred to have at least one modulator nanoparticle present for approximately every 10 kb of a nucleic acid, and more preferably for every 1 kb, and most preferably for every 500 bp.

The effect of a nanoparticle on nucleic acid hybridization is demonstrated in Examples 2–4. These non-limiting examples show that induction heating of a nanocrystal can dehybridize double stranded DNA. Induced dehybridization occurs on the time scale of seconds. Furthermore, induction heating is localized and can be used to dehybridize DNA selectively. In addition, induction heating can control biomolecules such as nucleic acids in a switch-like manner, so that biomolecular switches can be produced in solution.

Selective dehybridization can be employed to numerous ends. In one implementation, an oligonucleotide complementary to a portion of an mRNA molecule binds to the complementary portion in order to inhibit translation. Association of a modulator with the oligomer permits hybridization to be defeated (i.e., the oligomer and the RNA are dehybridized, or hybridization is prevented altogether) upon application of the excitation field. This type of system is useful, for example, in synchronizing translation events across many ribosomes in order to facilitate detection of the protein product.

In another application, a modulator is employed in conjunction with a nucleic acid that exhibits enzymatic activity, such as a ribozyme or DNA 10–32, an example of a DNA strand that was discovered to have catalytic activity. Transduction of energy into the molecule through activation of the modulator may be found to enhance or inhibit the enzymatic activity, depending on the context.

Figure 5:
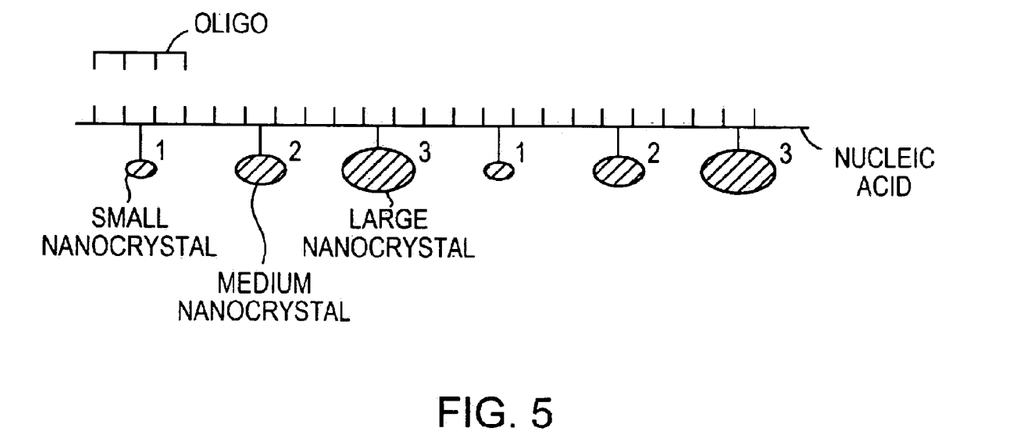
FIG. 5 is a schematic diagram illustrating multiple independently addressable control modulators attached to a single nucleic acid molecule.

In still another application, different molecules (or regions of the same molecule) are addressed independently by using modulators having different addressability characteristics (FIG. 5). This may be achieved, for example, by using chromophores having different absorption characteristics, or by using differently sized conductive nanoparticles (which have different resonant heating frequencies). Such a system may be used, for example, to create a molecular stepper motor. The basic idea of the molecular stepper motor is to create repeating sets of independently addressable regions on a single-stranded polymer of nucleic acid (or a functionally equivalent molecule). The illustrated polymer has repeating sequences of nucleic acids and there is a free oligonucleotide complementary to the repeating sequence. Initially all modulators are off and the oligomer binds randomly to some region of the polymer. Now RF is applied to modulators 1 and 2. If the oligomer is bound to one of the regions addressed by the hot modulators (i.e., 1 or 2) it will be forced to dehybridize and move to a colder region (i.e., the region of the unenergized modulator 3). By now applying RF to modulators 2 and 3, the oligomer is forced to move to the region underneath modulator 1. By continuing in this fashion one can cause the oligomer to "step" along the polymer programmatically.

Figure 6:
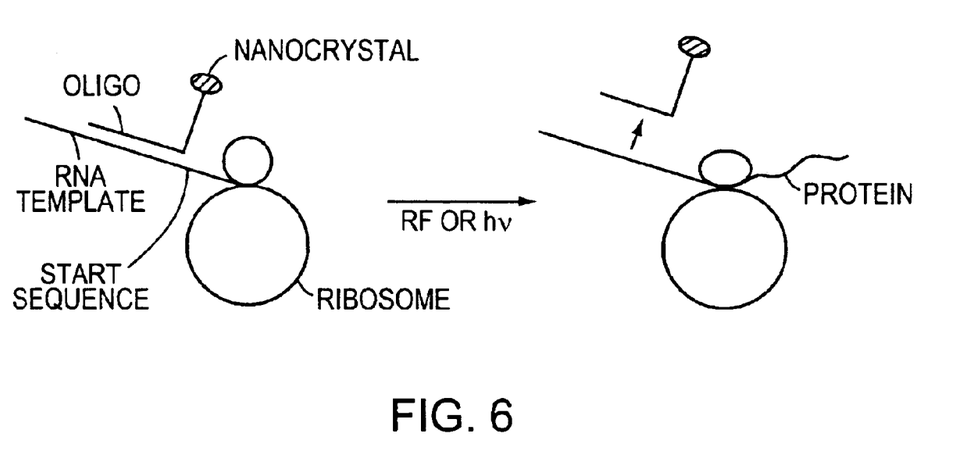
FIG. 6 is a schematic showing control of gene expression by controlling hybridization to an RNA template.

In yet another application, shown in FIG. 6, transcription of a protein by a ribosome from an RNA template may be controlled by means of an oligomer complementary to an RNA template (antisense) and having a modulator bound thereto. In the absence of an excitatory signal the oligomer is bound to the RNA, thereby precluding transcription. However, upon application of, e.g., an RF pulse, the oligomer is dehybridized, allowing transcription to commence. Such a system may be useful in controlling gene expression generally, or in synchronizing transcription events across many ribosomes (e.g., for purposes of readout, as discussed below, if it is impractical to read a signal from a single mRNA).

Figure 7:
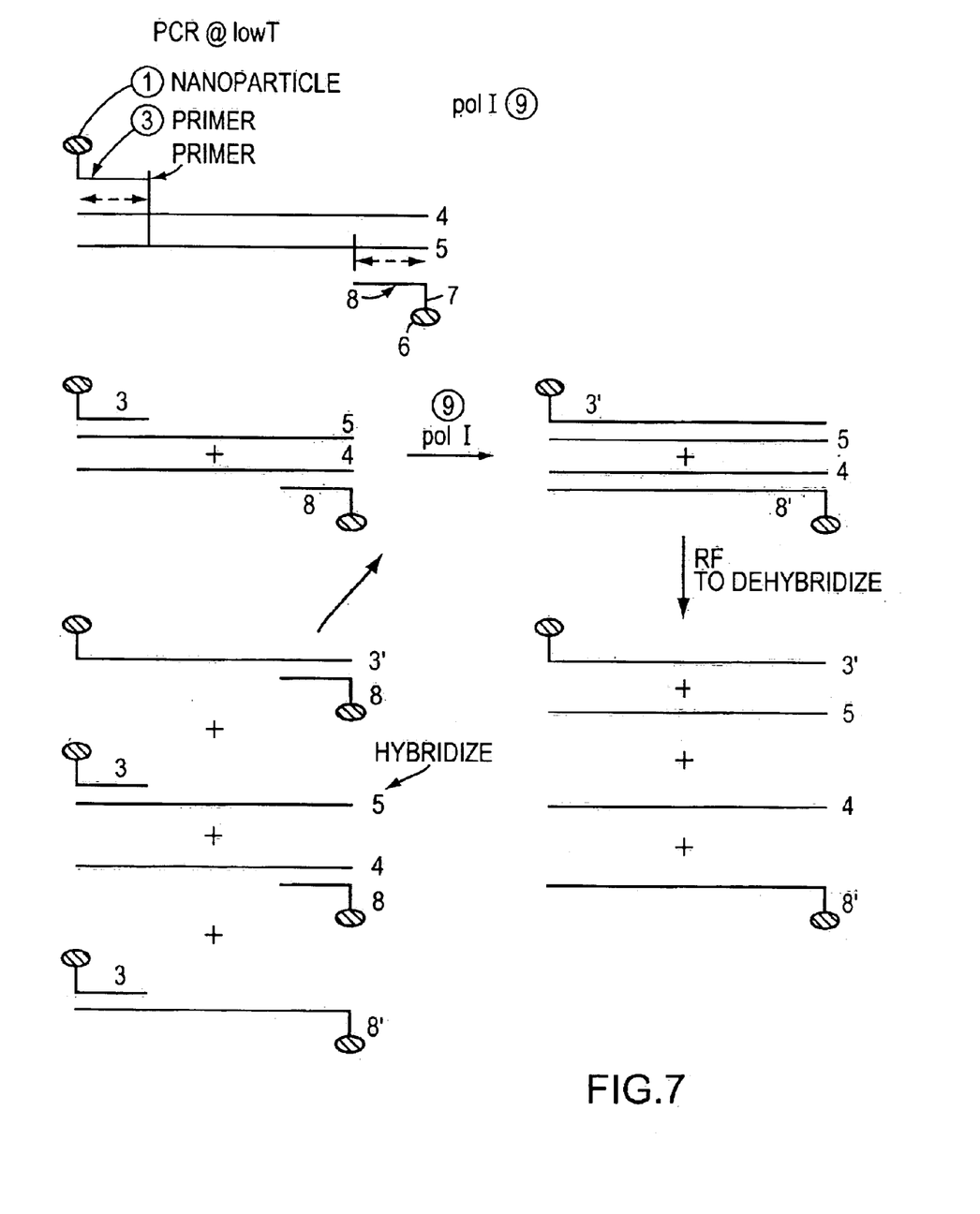
FIG. 7 schematically illustrates geometric amplification of nucleic acids according to the present invention.

Modulators may be used in connection with copying and amplification reactions in order to avoid the need to vary the temperature of the entire environment in the course of the reaction cycle (FIG. 7). The standard components of a polymerase chain reaction (PCR) reaction are a template nucleic acid, all four deoxynucleotides, synthetic oligonucleotide primers, buffer and a thermo-stable polymerase. Conventional PCR reactions proceed by cycling the chemical components through three temperature phases: denaturation, annealing and extension. In a conventional polymerase chain reaction, a DNA segment to be copied is first denatured into single strands by heating (to 95° C.). Excess amounts of two synthetic oligonucleotides complementary to the 3' ends of the DNA strands are added to the denatured DNA, and the mixture incubated by lowering the temperature to the annealing point (50–60° C.). At this temperature the oligomers hybridize with the DNA strands. The hybridized oligonucleotides serve as primers for DNA chain synthesis, which begins upon addition to the reaction mixture of deoxynucleotides and a temperature-resistant DNA polymerase (such as Taq polymerase). When synthesis is complete, the mixture is reheated to the denaturation temperature to melt the newly formed DNA duplexes. Lowering the temperature causes the oligomers, which are still at a high relative concentration, to bind to the denatured DNA strands, and another round of synthesis takes place.

In accordance with the present invention, modulators are used to control the PCR reaction, either by direct local heating of the subject molecules or simply through dispersion in the reaction mixture. In the former case, modulators are linked to the primer oligomers, and the temperature of the reaction mixture is maintained at the incubation point. Following DNA synthesis, the excitation field is applied, dehybridizing the newly formed duplexes. Because the reaction mixture as a whole remains at the incubation temperature, the next cycle of synthesis begins as soon as the field is deactivated, and this sequence is repeated to produce the desired degree of amplification.

The use of modulators to directly heat the molecules being amplified in a nucleic acid amplification reaction, rather than global temperature changes, offers numerous benefits. First, the polymerase need not be heat-resistant, since the reaction temperature does not change substantially. This facilitates use of polymerases (such as PolI or the Klenow fragment) able to proofread the new strands, thereby reducing duplication errors. The ability to avoid large reaction temperature changes also simplifies equipment arrangements, and can reduce overall reaction times.

If the modulators are simply dispersed in the reaction mixture (instead of bound to the primers), excitation is essentially employed to raise the temperature of the reaction mixture in order to induce dehybridization.

Different modulators having different excitation characteristics can be employed on the same molecule or on different molecules. For example, chromophores each having a different $\lambda_{max}$ can be attached to the same nucleic-acid molecule. Their selective activation, through application of radiation at one or more of the $\lambda_{max}$ wavelengths, will preclude hybridization with an oligomer at the affected region or regions. The same effect may be produced using metal, semiconductive or magnetic nanocrystals having different resonant frequencies. By locating the differentially responsive modulators at various spaced-apart points along the length of the nucleic-acid molecule and selectively activating them, hybridization can be prevented at selected regions (or caused to occur at a specific region through activation of modulators at all other eligible regions). Indeed, an oligomer can be caused to "step" down the length of the nucleic acid as selected modulators are excited (as discussed in greater detail below).

3. Readout

Figure 8:
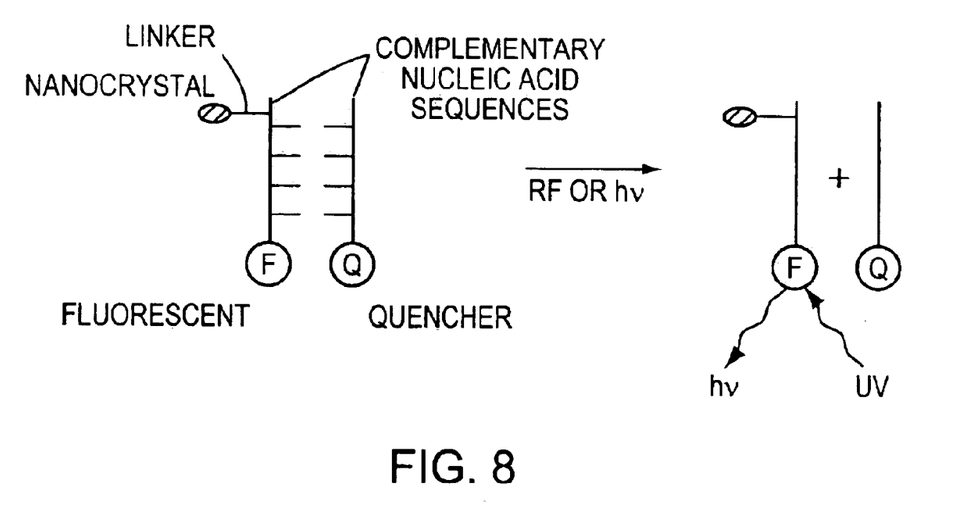
FIG. 8 schematically illustrates a system for optically reading out the state of a molecular system or application of a control input to a molecular system.

The invention can be used to detect—i.e., "read out"—the state of a molecular system or the action of a control input into a molecular system. This may be accomplished optically, by means of nuclear magnetic resonance, or through direct electronic means. FIG. 8 illustrates readout of change in hybridization through the use of a fluorescer-quencher pair. The emitter molecule is attached covalently to one of the two nucleic acids, and the quencher molecule is attached to the other. The emitter and quencher are situated near each other such that when the system is hybridized, it is dark due to non-radiative energy transfer between the fluorescer and quencher. Upon dehybridization caused by application or RF or a light pulse, the quencher molecule is far from the fluorescer and thus emission is detectable. Once again the modulator may be a metal, semiconductor, or magnetic nanocrystal, or optical chromophore. The nucleic acid may be a DNA, RNA or PNA oligomer, or other structure forming molecules covalently linked to the modulator. The fluroescent molecule may be, for example, FAM or R6G. The quencher molecule may be, for instance, DABCYL.

With reference to the structure shown in FIG. 8, the readout means may be quantum dots which are either quenched by a quencher or which change their fluorescent properties based on upon the presence or absence of a bound molecule. A gold nanoparticle, for example, may be used as a quencher.

NMR can also be used to detect protein activity. For example, subjecting structures that contain a conducting nanoparticle to an AC magnetic field induces an eddy current in such nanoparticles. This eddy current in turn generates its own magnetic field, which, because it is highly localized, may be used to increase the NMR signature from a nearby NMR-active atom such as gadolinium or from another molecule. The effect may be further enhanced by incorporating a nano-ring in place of a nanoparticle. This is similar to the focusing coils used in MRI equipment but at a vastly reduced length scale.

In many of these schemes for readout it may be difficult or impossible to read from a single molecule. An important general approach enabled by modulators is the ability to synchronize the output from many biomolecules simultaneously so that their collective output may be detected. This may facilitate, for example, determination of the concentration of a particular species, or the sequence of nucleotides being transcribed by a polymerase. A modulator can, for example, be used to commence the transcription process simultaneously in many polymerases such that a signal, e.g., from a Gd atom positioned on the polymerase, can be detected and the sequence "read out."

4. Cooling

The mean molecular temperature of a biomolecule may be lowered (rather than increased) relative to its surroundings by attaching a magnetic nanoparticle to the biomolecule of interest, such as a nucleic acid. Such a magnetic particle may be used in a superparamagnetic cooling arrangement in which the magnetic moment of the nanoparticle is first polarized in a magnetic field and then allowed to dephase using energy contained in the biomolecule, thus cooling the biomolecule. In order to achieve efficient cooling the magnetic nanoparticle should be thermally decoupled from the biomolecule during the polarization step. This may be accomplished by initially breaking a bond between the magnetic nanoparticle and the biomolecule with a laser or other means, then facilitating magnetic polarization, which allows the bond to reform.

This invention is further illustrated by the following non-limiting examples.

EXAMPLES

Example 1

Methods and Compositions for Associating Modulators with Nucleic Acids

DNA oligonucleotides were purchased from Research Genetics with end modifications of biotin, primary amines, or 6-carboxyfluorescein (FAM). Exposure of fluorescently labeled oligonucleotides to light was minimized to prevent photobleaching. All oligonucleotides were HPLC purified.

a) Labeling an Oligonucleotide with a Gold Nanocrystal.

All DNA oligonucleotides were synthesized via solid phase chemical synthesis (Research Genetics, Huntsville). Addition of internal amines, terminal biotin, or fluorophores was done during oligo synthesis. Oligo M: DNA loop/hairpin oligos ("molecular beacons") have a thymine in the loop region which was modified on the 5 position of the base with a C6 primary amine, to which a nanocrystal was covalently linked. Functionalized 1.4 nm gold nanocrystals which have a single sulfo N-hydroxy-succinimide (NHS) ester and are uncharged (Nanoprobes, Yaphank, N.Y.) were incubated with the oligo in the manufacturer's buffer solution at room temperature for 1 hour, resulting in a covalent bond between the nanocrystal and the oligo. The nanocrystals were in large molar excess (>10×). Excess nanocrystals were removed by 70% ethanol precipitation on ice and by repeated washes. The nanocrystals were soluble in ethanol but the DNA, or species attached to DNA, precipitated. The concentrations of oligonucleotides M and N was 1×10-nM in 1× PBS (phosphate buffer solution=1 mM $KH_2PO_4$, 10 mM $Na_2HPO_4$, 137 mM NaCl, 2.7 mM KCl).

b) Immobilizing DNA on a Solid Support (Two-phase System)

Oligo X is a 12mer that has a 6-carboxyfluorescein (FAM, $\lambda_{max}$=516 nm) on the 5' end and a 1.4 nm gold nanocrystal on the 3' end ($T_m$=40° C.). It was labeled with the nanocrystal as described above. Oligo Y is a 68mer complementary to X and has a biotin on the 5' end. Oligo X was labeled with a nanocrystal as described above. The oligos X and Y were hybridized, and the X-Y hybrid was incubated with streptavidin agarose beads (Sigma-Aldrich) with <d>=100 μm to allow the biotin on the Y to bind to the streptavidin. Samples were washed several times with 1× PBS to remove free gold. This biotin-streptavidin reaction is nearly covalent ($K_d$=$10^{-15}$ M) and remains intact for temperatures across those used in the experiments. Previous experiments in which bead-bound Y was heated to 85° C. showed no presence of the oligonucleotide in the supernatant, confirming that the biotin-streptavidin interaction was robust over these temperatures.

Figure 2A:
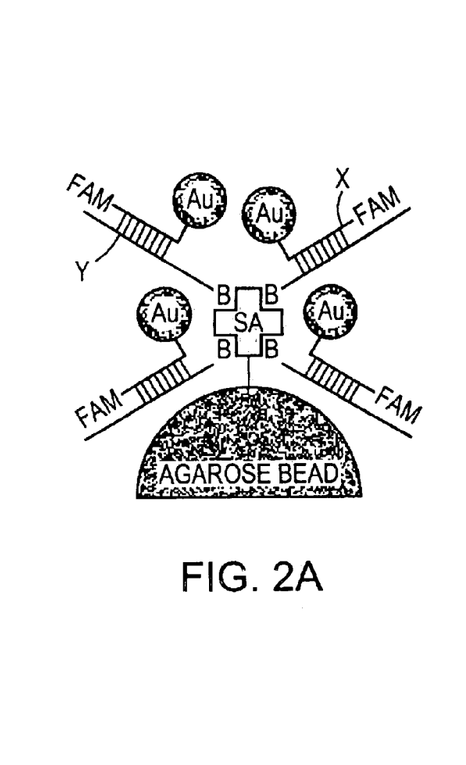
FIG. 2(a) shows an oligonucleotide of 12 nucleotides ($T_m$=40° C.) that is covalently linked to a gold nanocrystal on the 3' end and has 6-carboxyfluorescein (FAM, $\lambda_{max}$=516 nm) on the 5' end (gray strand)
Figure 2B:
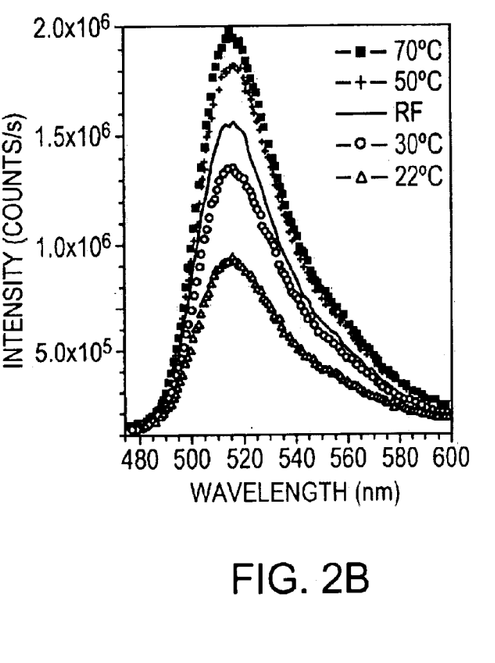
FIG. 2(b) shows fluorescence spectra of the supernatant of the system shown in FIG. 2(a) after exposure to heat or an RFMF.
Figure 2C:
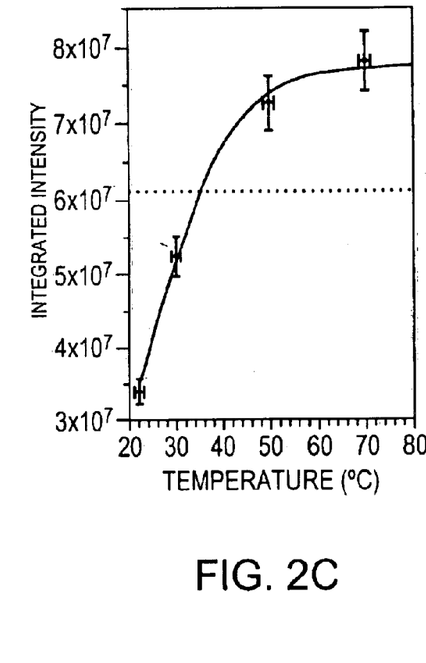
FIG. 2(c) shows the integrated peak intensity of the supernatant fluorescence spectra shown in FIG. 2(b)

In the construction of the two-phase system in FIG. 2, X was purified from the unlabeled oligos by exposing the bead-immobilized X-Y to the RFMF. The RFMF dehybridized only those oligos that are linked to a nanocrystal. Oligos not linked to a nanocrystal had no response to the RFMF and thus remained hybridized to Y. Purification was confirmed by an increase in ratio of oligos that dehybridize in the presence of RFMF to the total number of oligos in the sample (measured by exposing the sample to 85° C., not shown). This is another alternative to purification by gel electrophoresis, which is not effective for separating 12 nucleotide oligos attached to gold nanocrystals from the free nanocrystals.

Purified oligo X was hybridized to Y, and subsequently exposed to streptavidin coated agarose beads (<d>=100 µm) in order to immobilize the hybrids. After washing away free oligos with 1× PBS, additional buffer was added to the beads to serve as the liquid phase. Samples were exposed to the RFMF or globally heated at a specific temperature. Following heating or exposure to the RFMF, the supernatants were separated from the beads and measured by fluorescence spectroscopy. All fluorescence spectra were taken under identical conditions (temperature, spectrometer parameters).

c) Labeling an Oligonucleotide with a Second Fluorophore (Mixed Two-phase System).

Oligo Z was identical in sequence to X but was labeled on the 3' end with NHS-tetramethylrhodamine (TMR, Molecular Probes, Eugene, Oreg.). Attachment of the TMR to the primary amine on Z was performed according to the manufacturer's directions, which were to incubate the two molecules in sodium bicarbonate solution for 1 hour at room temperature in the dark in order to prevent photobleaching of the TMR. Oligo Z was hybridized to oligo Y, mixed in solution with the X-Y hybrid, and then incubated with tetrameric avidin coated acrylic beads (Sigma-Aldrich) as described in section 3. Free molecules were removed with multiple washes of 1× PBS. The sample resulted in equimolar amounts of X to Z on the acrylic beads. The surface density of the monomeric avidin on the bead is roughly one molecule/1 $nm^2$, and at the concentrations used, this results in ~2% of the avidin sites being occupied by hybrids.

d) Applying a RFMF

Alternating magnetic fields were generated by applying an alternating current to a coil with 35 turns and an area of ~1 $cm^2$. Coils were wrapped around plastic cuvette/tube holders that had an open structure so as to maximize the passage of light. Currents with frequencies in the radio frequency range were obtained by using an RF signal generator (Hewlett Packard 8648C) with an output of 1 mW in conjunction with a linear amplifier. The ultimate output power range used was from 0.4 W to 4 W, though these are considered to upper limits to the exact power inside the coil due to losses from setup architecture. The DNA hairpin samples were put into a 3 mm x 3 mm quartz cuvette inside the coil and had a volume of 200 µl, and the power used for the sample in FIG. 1 was 4 W. Samples for the two phase system were put in the coil in 200 µl plastic PCR tubes with a supernatant volume of 165 µl and a solid phase volume of 60 µl. The power used in FIG. 2 was 4 W and FIG. 3 was 1 W.

e) Spectroscopy

The UV/visible data was taken on a DU530 Beckman spectrophotometer with a time resolution limited to 5 s steps. Fluorescence spectra was taken on a Spex Fluoromax fluorometer with 1 nm steps and entrance/exit slits at 1.5 nm. Signal was averaged multiple times (7) in order to get a reasonable signal: noise ratio. Fluorescence peak areas were quantified by Voigt lineshape deconvolution using a commercial program (Peakfit, SPSS, Inc.)

Example 2

Direct Inductive Heating of an Oligonucleotide Associated with a Gold Nanocrystal in Solution Inductive coupling involves the transfer of energy from one circuit to another. If the secondary circuit has a finite impedance, eddy currents are produced which are converted to heat by the Joule effect. This technique of heating a conductor by placing it in an alternating magnetic field is generally used to heat macroscopic samples (centimeter length scales). Here, metallic nanocrystals (diameter≈1.4 nm) are applied in solution. Induction heating is accompanied by a skin deep effect resulting from partial cancellation of the magnetic fields. As a result, the majority of the power absorbed by a conductor is concentrated in a depth $d_0$ given by $$d_0 = \frac{1}{2\pi}\sqrt{\frac{\rho \cdot 10^7}{\mu_r \mu_0 f}} \quad (1)$$

where $\mu_r$=magnetic permeability, $\mu_0$=permeability of free space, ρ=material resistivity, and f=frequency of the alternating magnetic field. The power density is described by $$P = 4\pi H_e^2 \mu_0 \mu_r f F \frac{d_0}{d} \quad (2)$$

where d=sample diameter, $H_e$=magnetic field strength, and F is a transmission factor that has a sigmoidal dependence on (d/$d_0$). This results in optimal power absorption or heating when d/$d_0$=3.5. To inductively heat a gold nanocrystal with d=1.4 nm such that d/$d_0$=3.5, alternating magnetic fields with f=50 GHz (radio frequency range) are required.

Figure 1A:
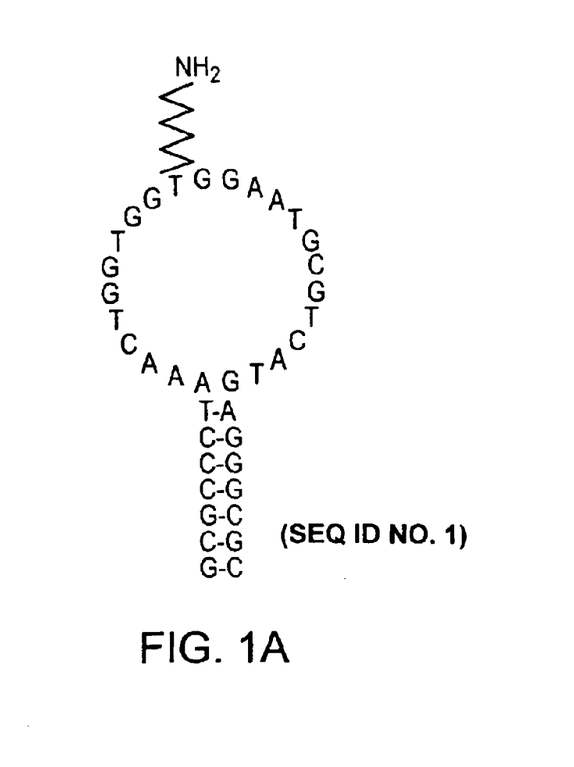
FIG. 1(a) shows the sequence of a DNA hairpin molecule (SEQ ID NO.1) that can be dehybridized by induction heating of a gold nanocrystal.
Figure 1B:
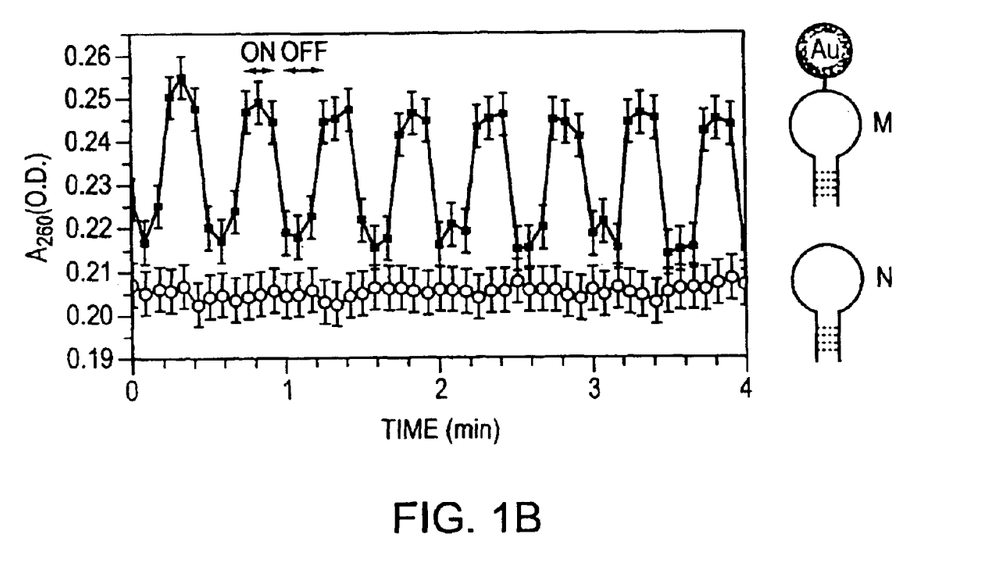
FIG. 1(b) shows absorbance at 260 nm as a function of RFMF switching; the upper curve shows the response of a DNA hairpin oligonucleotide linked to a 1.4 nm gold nanocrystal; the lower curve shows the response of a DNA hairpin oligonucleotide without a gold nanocrystal.

In order to demonstrate reversible, electronic control, a DNA hairpin-loop oligomer covalently linked to a nanometer-scale antenna was constructed. 38mer DNA hairpin/loop oligos which are self-complementary at each end for 7 bases (FIG. 1a) were covalently linked to a 1.4 nm gold nanocrystal by a primary amine appended to one of the bases. Because of the constraint of the loop, the DNA rehybridizes on a timescale comparable to dehybridization. The amount of dehybridization was monitored by the hyperchromicity of DNA, which was measured by optical absorbance at 260 nm ($A_{260}$). A solution of the nanocrystal-linked oligos (oligo M) was put into a radio frequency magnetic field (RFMF) with f=1 GHz. Although this frequency is not optimal, it still results in heating of the nanocrystals. $A_{260}$ was monitored in a UV/visible spectrophotometer as the RFMF was pulsed at 15 s intervals (FIG. 1b). As the RFMF was switched on, $A_{260}$ increased from 0.22 to 0.25 OD, indicating that M dehybridized with the RFMF (squares). When the RFMF was switched off, $A_{260}$ returned to its original value. Cycling through the on and off states was completely repeatable. The on/off ratio of $A_{260}$ is 1.09, consistent with calculated absorption coefficients for an oligo of this sequence hybridizing and dehybridizing 7 bases. Control solutions with only DNA (oligo N) resulted in no change in the absorbance with RFMF (circles). This demonstrated that inductive coupling to a covalently bound metal nanocrystal can reversibly dehybridize DNA on a timescale of at the most several seconds.

Example 3

Direct Inductive Heating of an Oligonucleotide Associated with a Gold Nanocrystal on a Solid Support To determine the effective temperature that inductive coupling to the nanocrystal antenna produces in its local environment, a two-phase system was designed in which an oligo is dehybridized from a solid support into solution (FIG. 2a). Oligo X is a 12mer with a nanocrystal on the 3' end and a fluorophore (FAM) on the 5' end. It was hybridized to its complement, oligo Y, which was immobilized on 100 µm streptavidin coated agarose beads that comprise the solid phase. When X was dehybridized from Y, it diffused from the solid phase to the supernatant. The amount of dehybridization was proportional to the amount of X in the supernatant, which was measured by fluorescence spectroscopy. One sample was exposed to the RFMF and its supernatant was removed. Its fluorescence spectrum was compared to supernatants of identically prepared samples that were thermally heated at specific temperatures. The supernatant fluorescence spectra (FIG. 2b) showed that the FAM intensity increased with temperature, indicative of increased amounts of X dehybridized. The sample exposed to RFMF (solid line) had an intensity in between that of the 30° C. and 50° C. samples. The integrated peak intensity of the spectra (FIG. 2c) as a function of incubation temperature (squares) was fitted to a sigmoidal (solid line), corresponding to a thermal denaturation curve. From the intensity of the RFMF sample (dashed line) the extrapolated temperature was 35° C., indicating that the effective temperature that the RFMF produced on X is ~13° C. above the ambient temperature. This change in temperature is sufficient for control of many processes within biology.

Example 4

Figure 3A:
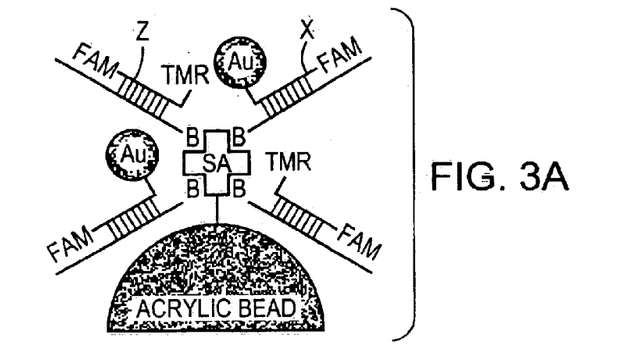
FIG. 3(a) shows a system used to test selective heating in accordance with the invention.
Figure 3B:
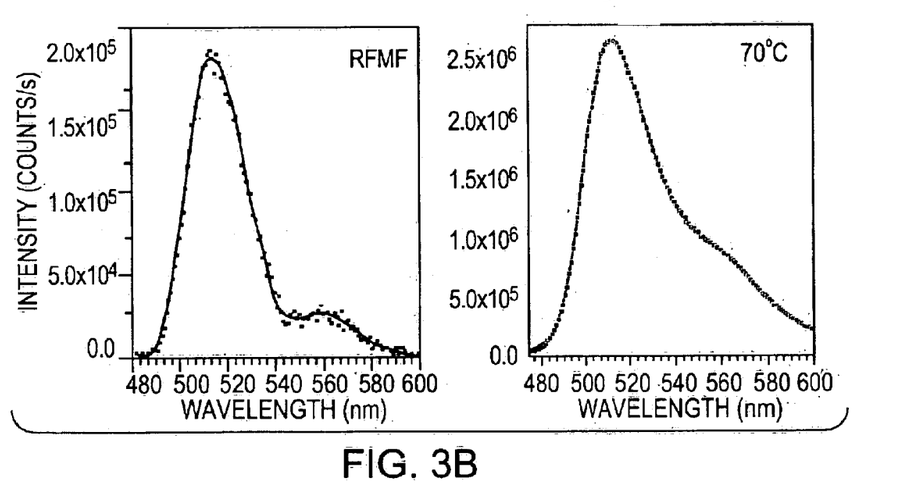
FIG. 3(b) shows fluorescence spectra of the supernatant of a sample before (dotted line) and after (solid line) exposure to an RFMF (3(b) left) or heat (3(b) right).
Figure 3C:
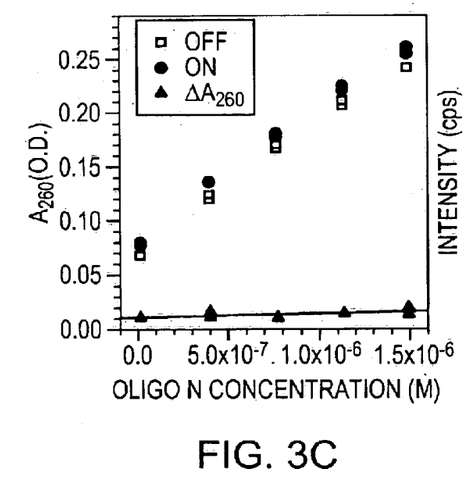
FIG. 3(c) shows the difference in absorbance at 260 nm of a mixture of two oligonucleotides with the RFMF on (solid circles) and off (empty squares) and the difference in absorbance (filled triangles) and fit (line) as a function of the concentration of one of the oligonucleotides.

Selective Inductive Heating of an Oligonucleotide Associated with a Gold Nanocrystal An important feature of the invention is the ability to address molecules with an antenna selectively while having a lesser effect on molecules which are not bound to a nanocrystal antenna. In order to demonstrate selective dehybridization a two-phase system was used in which X was mixed with Z, an oligo which had no nanocrystal attached (FIG. 3a). Z is identical in sequence to X but has TMR on the 3' end, which emits at a wavelength distinct from FAM ($\lambda_{max}$=563 nm). The two-phase system is comprised of tetrameric avidin acrylic beads with both X-Y and Z-Y hybrids on the surface in approximately equimolar amounts. One sample was exposed to the RFMF and the supernatant was compared to a thermally heated sample (70° C.) by fluorescence spectroscopy. The difference of the spectrum before and after dehybridization for the 70° C. sample (FIG. 3b, right) had peaks at both 515 nm and 563 nm, indicating dehybridization of both X and Z. The RFMF spectrum (FIG. 3b, left) showed increased intensity at 515 nm due to dehybridized X but negligible change in intensity at 563 nm, which indicated its selectivity. Quantification of the spectra yielded the percentage of X in the supernatant as being ~80% for the RFMF sample, while for the 70° C. sample it was ~55%. The slight amount of Z that was dehybridized in the RFMF sample was most likely a consequence of the proximity of the two types of molecules associated with the tetrameric avidin (where intermolecular separation is expected to be $\geq$10 nm). As the source of heat was from a nanometer scale antenna, Z was relatively unaffected by induction heating of X in its proximity. RFMF experiments on solutions of mixtures of unlabeled and labeled hairpin oligos also illustrate selective heating. FIG. 3c shows the $A_{260}$ with the RFMF on and off for a fixed concentration of M as N was added. $A_{260}$ on and off values increased linearly, but the difference ($\Delta A_{260}$) remained constant. Samples of increasing concentration of M showed $\Delta A_{260}$ increasing with the concentration (not shown).

Figure 3D:
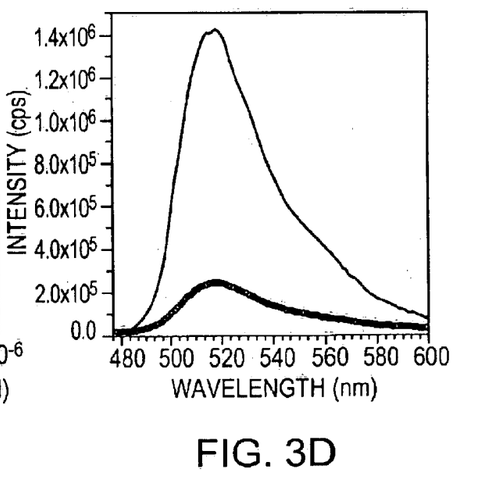
FIG. 3(d) shows spectra of supernatants with one (circle) or two (line) RFMF dehybridizations normalized to the intensity of the 70° C. aliquot for each sample.

These experiments indicated that induction heating of a nanocrystal on M is sufficiently localized in that N is unaffected. A third test of selectivity of RFMF dehybridization was evident in the purification of gold-linked X from unlabeled X where a fraction of gold-linked oligomers increased with successive dehybridization by RFMF. FIG. 3d shows the fluorescence spectra of a sample after one and two RFMF dehybridizations, each normalized to thermal dehybridization by 70° C. which provided the total amount of oligomers present. The percentage of molecules dehybridized by RFMF increased with the second cycle, indicating that the RFMF preferentially dehybridizes oligomers linked with gold nanocrystals. These experiments showed that induction heating of the nanocrystal is sufficiently localized such that surrounding molecules are not substantially affected.

These experiments also demonstrate the use of inductive coupling to a covalently bound nanocrystal antenna to reversibly dehybridize double stranded DNA on the time scale of seconds, permitting a switch-like control in solution. Furthermore, induction heating is sufficiently localized to permit selective dehybridization, and is used to purify nanocrystal labeled oligos from unlabeled oligos.

Manipulation of DNA by itself is useful as an actuator and in performing computations. Control of dehybridization of antisense oligomers in transcription permits reversible control of the production of specific RNA messages. Because selective addressing through nano-antenna is not optical, but electrical, this RFMF biotechnology permits detection in highly scattering media. A broad range of applications for electronically controlled biology are anticipated.

Example 5

Control of Nucleic Acid Nano-assembler Using Modulators

Figure 4:
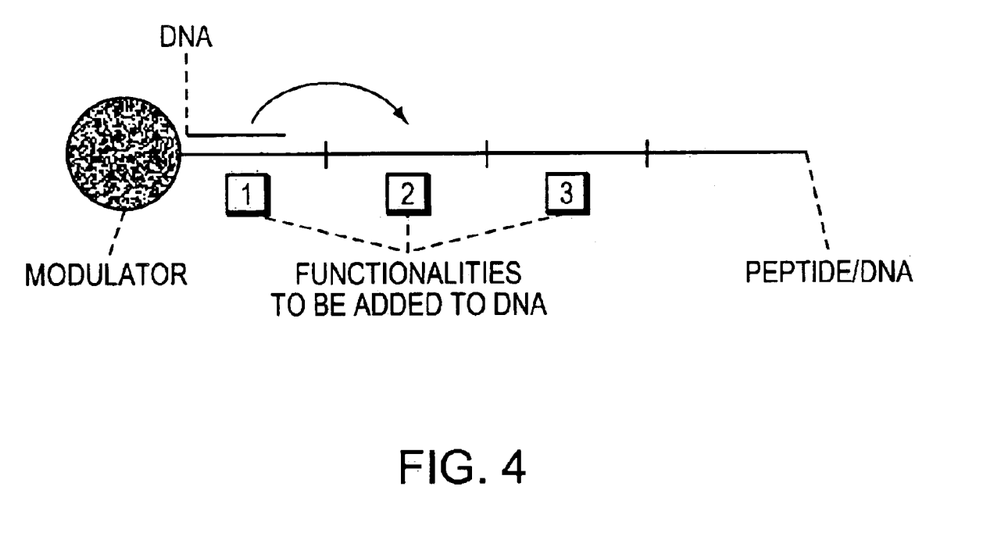

A modulator is attached to a series of modules (labeled 1, 2, 3), which are functionalities to be added to nucleic acids in a specific order (FIG. 4). Each module carries out a different function to build up a final product. The nucleic acid is transferred from module to module and its transfer is dictated by the sequence in which user addresses the various modulators by electromagnetic, magnetic, optical, or other physical means. The nucleic acid to be modified travels from module to module, each module carrying out a different function contributing to the final product. In another embodiment, the nucleic acid is attached to a bead that travels from module to module. This embodiment is especially useful for carrying out solid-phase synthesis on the bead (e.g., by means of an enzyme or other catalyst linked locally to each module). The user can program the arrangement of the modules by biochemical methods or reprogramming plasmids.

Although the present invention has been described with reference to specific details, it is not intended that such details should be regarded as limitations upon the scope of the invention, except as and to the extent that they are included in the accompanying claims.

What is claimed is:

1. A method for remotely altering a property of a nucleic acid or peptide nucleic acid, the method comprising the steps of:
  a) associating a nanoparticle with a nucleic acid; and
  b) exposing the nanoparticle to an external field, wherein the external field is selected from the group consisting of a magnetic field, an electric field, and an electromagnetic field, the external field causing localized heating or cooling of only a portion of the nucleic acid, altering the replication, transcription or translation properties of the nucleic acid.

2. The method of claim 1, wherein said nanoparticle is linked to said nucleic acid.

3. The method of claim 2, wherein said nanoparticle is covalently linked to said nucleic acid.

4. The method of claim 1, wherein said nanoparticle is selected from the group consisting of organic and inorganic nanoparticles that are responsive to an external field.

5. A method for remotely altering a property of a nucleic acid or peptide nucleic acid, the method comprising the steps of:
  a) associating a nanoparticle with a nucleic acid, wherein said nanoparticle is selected from the group consisting of metal nanoparticles, semiconducting nanoparticles, and chromophores; and
  b) exposing the nanoparticle to an external field, wherein the external field is selected from the group consisting of a magnetic field, an electric field, and an electromagnetic field, the external field causing localized heating or cooling of the nucleic acid, altering the replication, transcription or translation properties of the nucleic acid.

6. A method for remotely altering a property of a nucleic acid or peptide nucleic acid, the method comprising the steps of:
  a) associating a nanoparticle with a nucleic acid, wherein said nanoparticle is selected from the group consisting of non-colloidal gold, colloidal gold, silicon, ruthenium, cadmium selenide, gold maleimide, and hydroxysuccinimidyl gold; and
  b) exposing the nanoparticle to an external field, wherein the external field is selected from the group consisting of a magnetic field, an electric field, and an electromagnetic field, the external field causing localized heating or cooling of the nucleic acid, altering the replication, transcription or translation properties of the nucleic acid.

7. The method of claim 1, wherein said nanoparticle transfers energy to said nucleic acid upon exposure to said external field.

8. The method of claim 1, wherein said nanoparticle heats said nucleic acid upon exposure to said external field.

9. The method of claim 1, wherein said nanoparticle cools said nucleic acid upon exposure to said external field.

10. A method for preparing a nucleic acid that is responsive to an external field, the method comprising the step of associating a nucleic acid with a nanoparticle that is responsive to an external field, wherein the external field causes localized heating or cooling of only a portion of the nucleic acid.

11. The method of claim 10, comprising the step of covalently attaching said nanoparticle to said nucleic acid.

12. A method for preparing a nucleic acid that is responsive to an external field, the method comprising the step of associating a nucleic acid with a nanoparticle that is responsive to an external field wherein said nanoparticle comprises a phosphoramidite and is attached to said nucleic acid via a chemical reaction, and wherein the external field causes localized heating or cooling of the nucleic acid.

13. The method of claim 11, wherein the step of attaching the nanoparticle to the nucleic acid comprises the steps of covalently attaching the nanoparticle to a nucleotide, and attaching the nucleotide to the nucleic acid in an enzyme-catalyzed reaction.

14. The method of claim 13, wherein said enzyme-catalyzed reaction is a template-based nucleotide polymerization reaction.

15. The method of claim 14, wherein said nucleotide is provided to a cell and said polymerization reaction occurs in vivo in said cell.

16. A method for preparing a nucleic acid that is responsive to an external field, the method comprising the step of associating a nucleic acid with a nanoparticle that is responsive to an external field, wherein said nanoparticle is functionalized with an ester, and wherein the external field causes localized heating or cooling of the nucleic acid.

17. The method of claim 1, wherein the nucleic acid exhibits enzymatic activity and the exposing step affects the nucleic acid's enzymatic activity.

18. A method for remotely altering a property of a nucleic acid or peptide nucleic acid, the method comprising the steps of:
  a) associating a nanoparticle with a nucleic acid, wherein said nucleic acid is an amplification primer;
  b) exposing the nanoparticle to an external field, wherein the external field is selected from the group consisting of a magnetic field, an electric field, and an electromagnetic field, the external field causing localized heating or cooling of the nucleic acid, altering the replication, transcription or translation properties of the nucleic acid;

c) mixing a template nucleic acid with said amplification primer having a nanoparticle associated therewith to form a reaction complex, said nanoparticle being responsive to the external field; and d) causing extension of said primer along said template nucleic acid to produce an extension nucleic acid hybridized with and complementary to said template nucleic acid;

wherein step b) of exposing said nanoparticle to an external field denatures said extension nucleic acid from said template nucleic acid; and, wherein repeating steps d) and b) produces multiple copies of said extension nucleic acid.

19. The method of claim 18, wherein said amplification primer is a first amplification primer and wherein a second amplification primer is added to said amplification reaction.

20. The method of claim 18, wherein said second amplification primer hybridizes to the extension product of said first amplification reaction.

21. The method of claim 18, wherein said nanoparticle is covalently linked to said amplification primer.

22. The method of claim 18, wherein said nanoparticle is covalently linked to a nucleotide that is incorporated into said extension product.

23. The method of claim 1, wherein said property affects an intermolecular interaction.

24. The method of claim 23, wherein said intermolecular interaction is selected from the group consisting of DNA/DNA, RNA/DNA, DNA/PNA, RNA/PNA, DNA/protein, RNA/protein, and PNA/protein interactions.

25. The method of claim 23, wherein said intermolecular interaction is nucleic acid hybridization.

26. The method of claim 1, wherein said nucleic acid is complementary to an RNA molecule.

27. The method of claim 26, wherein said nucleic acid is an oligomer, and wherein hybridization of the oligomer with the RNA molecule inhibits translation of the RNA molecule.

28. The method of claim 27, wherein said oligomer comprises an antisense molecule.

29. The method of claim 27, further comprising the step of providing the oligomer to a cell, thereby regulating translation in vivo in the cell.

30. A method for remotely altering a property of a nucleic acid or peptide nucleic acid, the method comprising the steps of:

a) associating a nanoparticle with a nucleic acid, wherein the nucleic acid comprises a peptide nucleic acid; and b) exposing the nanoparticle to an external field, wherein the external field is selected from the group consisting of a magnetic field, an electric field, and an electromagnetic field, the external field causing localized heating or cooling of the nucleic acid, altering the replication, transcription or translation properties of the nucleic acid.

* * * * *

SEQUENCE LISTING

<160> NUMBER OF SEQ ID NOS: 1

<210> SEQ ID NO 1
<211> LENGTH: 38
<212> TYPE: DNA
<213> ORGANISM: Artificial Sequence
<220> FEATURE:
<223> OTHER INFORMATION: DNA hairpin-loop oligonucleotide with a primary
      amine appended to one of the bases

<400> SEQUENCE: 1
gcgccctaaa ctggtggtgg aatgcgtcat gagggcgc                           38